United States Patent [19]
Leriche

[11] Patent Number: 5,300,076
[45] Date of Patent: Apr. 5, 1994

[54] PERCUTANEOUS BONE SCREW FOR SUPPORTING A STEREOTAXY FRAME

[75] Inventor: Bertrand Leriche, Paris, France

[73] Assignee: Societe de Fabrication de Materiel Orthopedique-Sofamore, Paris, France

[21] Appl. No.: 959,129

[22] Filed: Oct. 9, 1992

[30] Foreign Application Priority Data

Oct. 11, 1991 [FR] France ............................ 91 12571

[51] Int. Cl.⁵ ............................................. A61F 5/04
[52] U.S. Cl. ..................................... 606/73; 606/130; 411/395; 411/417
[58] Field of Search ............... 606/73, 72, 104, 65, 606/66, 130; 411/394, 395, 399, 417, 420

[56] References Cited

U.S. PATENT DOCUMENTS

| | | | |
|---|---|---|---|
| 4,042,342 | 8/1977 | Muenchinger | 428/585 |
| 4,175,555 | 11/1979 | Herbert | 606/73 |
| 4,537,185 | 8/1985 | Stednitz | 606/73 |
| 4,978,350 | 12/1990 | Wagenknecht | 606/72 |
| 5,122,132 | 6/1992 | Bremer | 606/72 |

FOREIGN PATENT DOCUMENTS

| | | | |
|---|---|---|---|
| 195455 | 3/1985 | European Pat. Off. | |
| 323429 | 12/1987 | European Pat. Off. | |
| 373733 | 12/1988 | European Pat. Off. | |
| 2382225 | 9/1978 | France | |
| 643131 | 5/1984 | Switzerland | |
| 1061807 | 12/1983 | U.S.S.R. | 606/73 |

OTHER PUBLICATIONS

World Patents Index Latest Section PQ, Sep. 7, 1982 Derwent Publications Ltd. London, GB; Class P31, AN 83-710140/28 & SU-A-955 916 (MATVEEV) Oct. 30, 1990.

World Patent Index Latest Section PQ, Apr. 23, 1982 Derwent Publications Ltd., London GB; Class P31, AN 83-D0221K/09 & SU-A-921 556 (Med Tech Res Inst) 7 Juillet 1980.

Primary Examiner—Stephen C. Pellegrino
Assistant Examiner—Guy V. Tucker
Attorney, Agent, or Firm—Woodard, Emhardt, Naughton, Moriarty & McNett

[57] ABSTRACT

The screw (1) comprises an end formed by a dog point (2) having a plane transverse surface (3) and a cylindrical lateral surface (4) connected to the plane surface (3) by a rounded annular radius (5), it also comprises a threaded part (6) contiguous with the dog point (2) in which a self-tapping zone (8) is made which terminates at the base of the dog point (2), a smooth cylindrical part (9) being moreover arranged between its threaded part (6) and its head (11). The smooth part (9) is connected to the head (11) by an inclined plane zone (12). The rounded dog point (2) makes it possible to hold back without harming any mucosa or aponeurosis situated behind a bone through which the screw passes. The smooth parts (9 and 12) avoid damage to the skin of the patient. This screw is intended to be positioned very precisely and to remain anchored in the patient for the whole time necessary for the planned investigations, which avoids repeated piercing of the cranium or of any bone at each examination.

6 Claims, 4 Drawing Sheets

FIG. 4
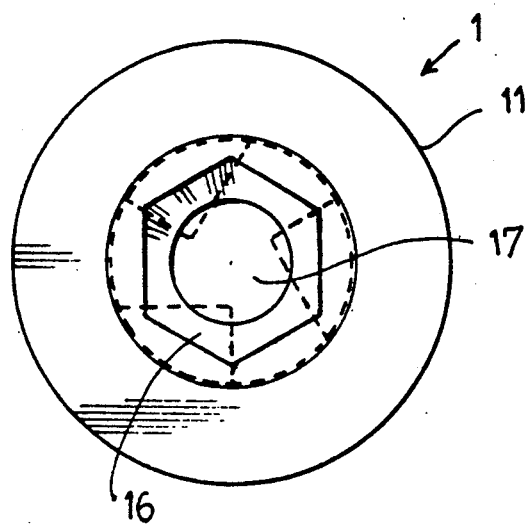
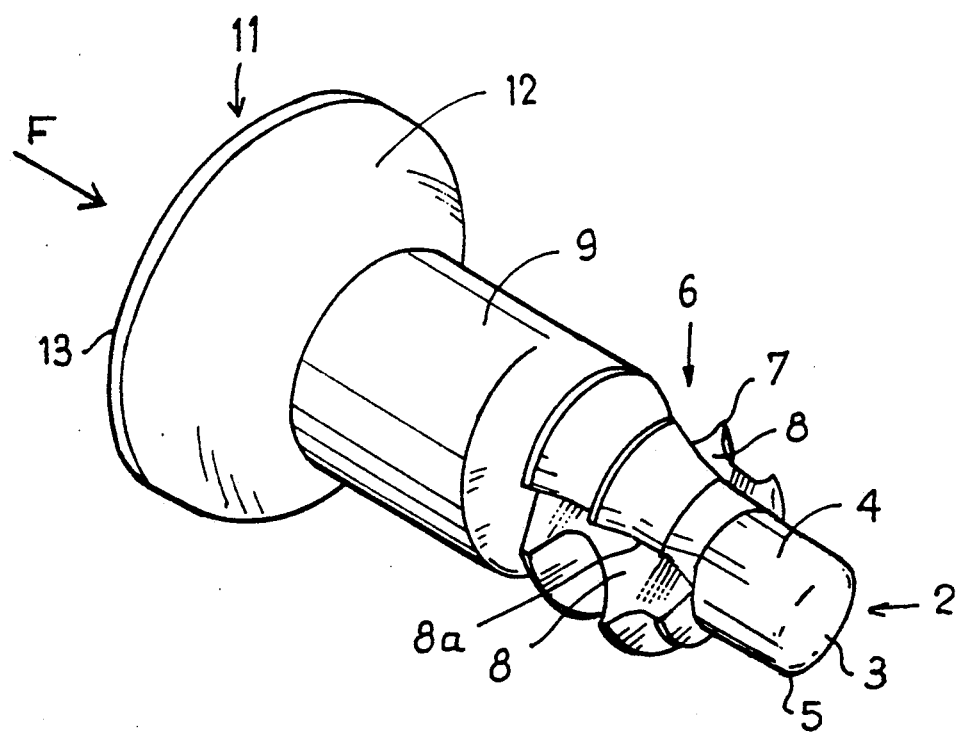
FIG. 3

PERCUTANEOUS BONE SCREW FOR SUPPORTING A STEREOTAXY FRAME

FIELD OF THE INVENTION

The subject of the present invention is a percutaneous bone screw, intended to support in particular a stereotaxy frame allowing investigation inside the neurocranium of a patient.

BACKGROUND OF THE INVENTION

The precise spatial reposition of the brain to millimeter accuracy is necessary for implementing certain therapeutic techniques, for example surgery in stereotaxic conditions, or repeated irradiation for tumour-related illnesses or vascular malformations (angiomas).

Positioning of a reference frame, which may or may not be metal, fixed to the neurocranium allows investigations to be performed in a topographically superposable manner: arteriography, ventriculography, body scanning, MRI, and performing treatments, which constitutes the principle of stereotaxy. But this assumes that the frame, and therefore the fastening of the cranial anchoring, is repositioned each time.

Two technical methods are possible for this purpose:
either a position-finding process which is redone each time, using three-dimensional coordinate computation. This computation is currently relatively easy but the refitting does not always have millimeter precision, taking into account that the needles of the frame are difficult to reposition in the holes of the bone.

This has obvious resulting drawbacks from the point of view of the patient: his neurocranium must actually be subjected to piercings, incisions of the scalp and local anaesthetics repeated on each refitting, giving rise to infection risks and painful discomfort. For the surgeon, repeating these fitting operations requires considerable time trying to find the position accurately.

Or precise repositioning, to millimeter accuracy, of the frame in the osseous structure of the neurocranium using percutaneous bone screws.

The latter technique, undoubtedly the most accurate, demands iterative refitting of the frame on the neurocranium, on percutaneous screws (that is to say, screws whose head projects out of the skin of the patient) which are anchored in the osseous structure, for several days on end or possibly several days per week for several weeks, during sequential irradiations.

SUMMARY OF THE INVENTION

The aim of the invention is therefore to provide a satisfactory solution to this problem, by producing percutaneous bone screw which can stay in place in the neurocranium of the patient after an initial accurate position-finding process, for several weeks for the purpose of investigation or therapy which can be well tolerated by the skin and bone, and allows iterative repositioning of the frame.

According to the invention, the percutaneous bone screw includes an end formed by a rounded and blunt dog point, and in its threaded part contiguous with the dog point, a self-tapping zone is made which is constituted by at least one groove formed by a flat bordered by sharp edges, and which terminates in the vicinity of the base of the dog point.

The rounded shape of the end of the screw avoids, during for example cranial anchoring of the screw, any risk of damage to the subjacent aponeurosis or mucosa such as the dura mater which forms an envelope for the brain. This membrane is actually slightly pushed back by the rounded dog point of the screw, ruling out any risk of oedema which could be caused by a cutting edge and limiting a possible inflammatory or haemorrhagic reaction.

The fact that the screw is provided with a self-tapping part avoids the necessity of boring and tapping the hole of the bone.

According to one possible embodiment of the invention, the dog point has a plane transverse surface and a cylindrical lateral surface connected to the plane surface by a rounded annular radius.

The screw advantageously comprises a cylindrical smooth part, arranged between its threaded part and a head adapted in order to receive a manipulating tool. This smooth part is transcutaneous when the screw is in place, for the purpose of the trophicity of the skin.

Other characteristics and advantages of the invention will appear during the description which follows, and which is made with reference to the attached drawings which illustrate an embodiment thereof by way of non-limiting example.

BRIEF DESCRIPTION OF THE DRAWINGS

FIG. 3 is a perspective view on the same scale as FIG. 1 and FIG. 2 of the percutaneous bone screw according to the invention.

FIG. 4 is a front view of the head of the screw along direction F of FIG. 3.

Figure 5:
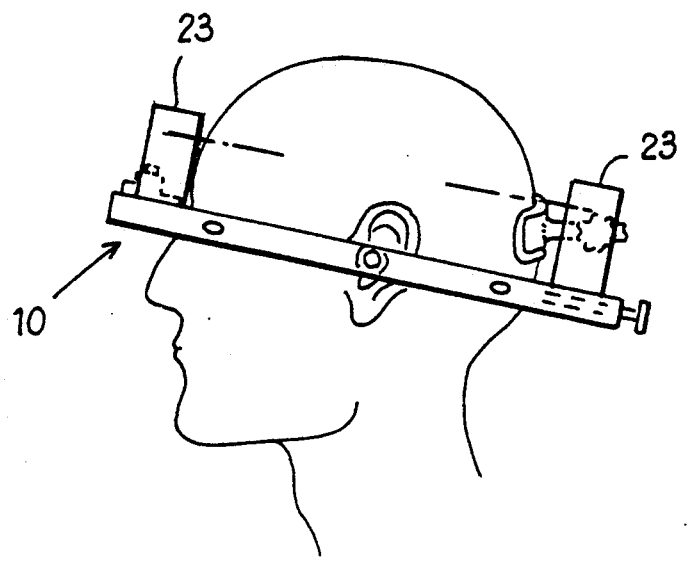
FIG. 5 is a schematic view in elevation of the head of a patient on which a stereotaxy frame is placed, this frame being supported by cranial screws according to the invention.
Figure 6:
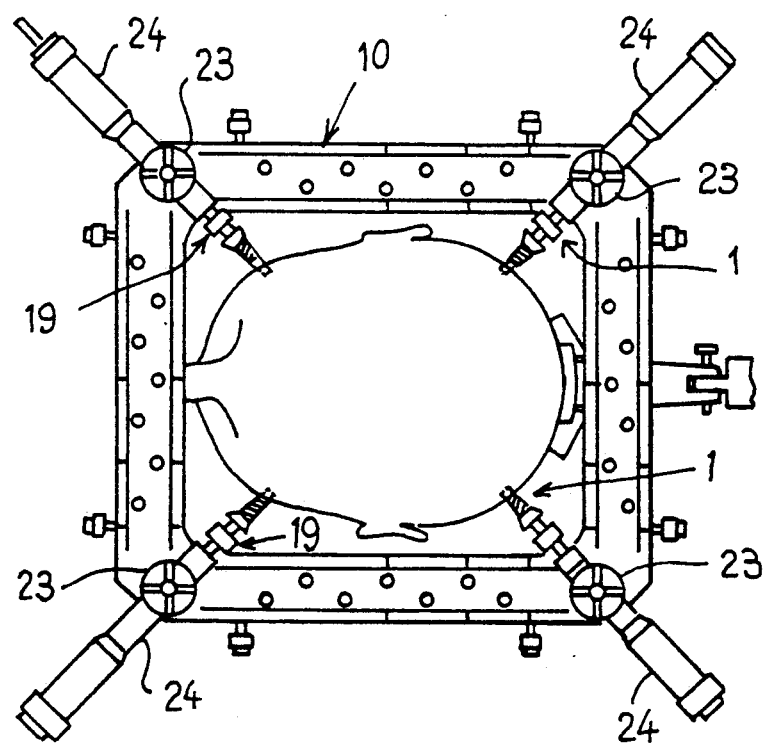
FIG. 6 is a view from above corresponding to FIG. 5, showing the positioning of the frame.

DESCRIPTION OF THE PREFERRED EMBODIMENT the percutaneous bone screw 1 represented in the drawings is intended to receive a support such as in particular a stereotaxy frame 10 (FIG. 5 and FIG. 6). It is capable of receiving other applications, for example for maxillo facial surgery or any subcutaneous bone surgery. In general, this bone screw is arranged in order to be able to hold back any mucosa or aponeurosis behind a bone, without causing damage to it.

The screw 1, with axis XX, comprises an end formed by a dog point 2 having a plane surface 3 transverse to the axis XX and a cylindrical lateral surface 4, connected to the plane surface 3 by a rounded annular radius 5. This screw also comprises a threaded part 6 fitted with threads 7, contiguous with the dog point 2 and in which a self-tapping zone 8 is made. This self-tapping zone is constituted by at least one groove formed by a flat 8, there being for example two as in the example represented, delimiting an interruption of the threads 7 and bordered by sharp edges 8a, these flats 8 terminating at the base of the dog point 2 or in the vicinity of the latter. The screw 1 furthermore comprises a cylindrical smooth part 9, arranged between its threaded part 7 and a head 11 which is adapted in order to receive a manipulating tool (screwdriver) which is not represented. The cylindrical smooth part 9 is connected to the head 11 by a plane annular zone 12, which is inclined to the axis XX and to the surface of the smooth part 9 by an appropriate angle. The annular zone 12 is connected to the transverse surface 13 of the head 11 by a cylindrical part 14 which is concentric with the axis XX.

Figure 1:
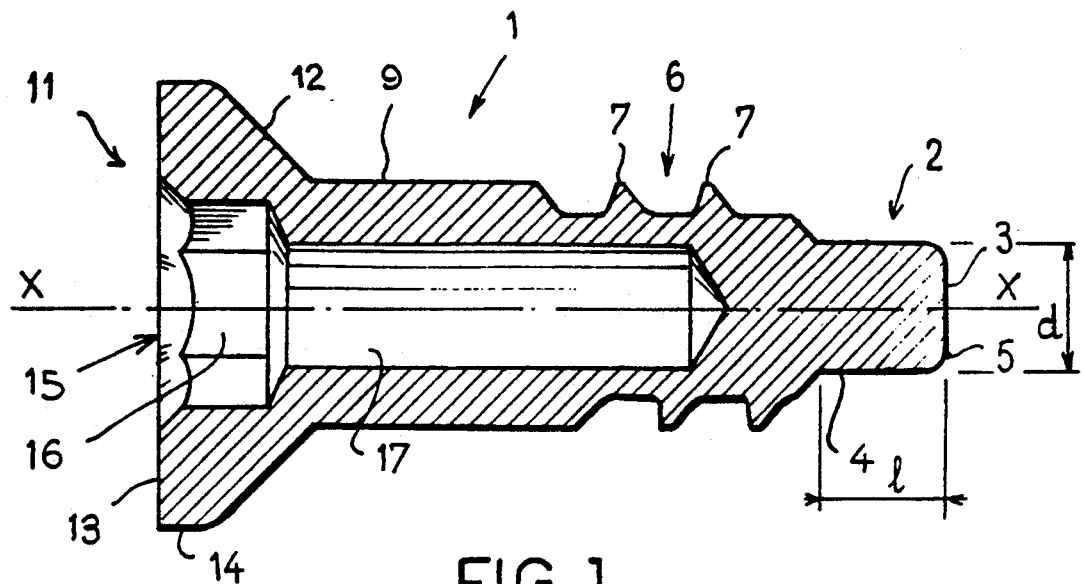
FIG. 1 is a view in axial section on a highly magnified scale, of an embodiment of the percutaneous bone screw according to the invention.
Figure 2:
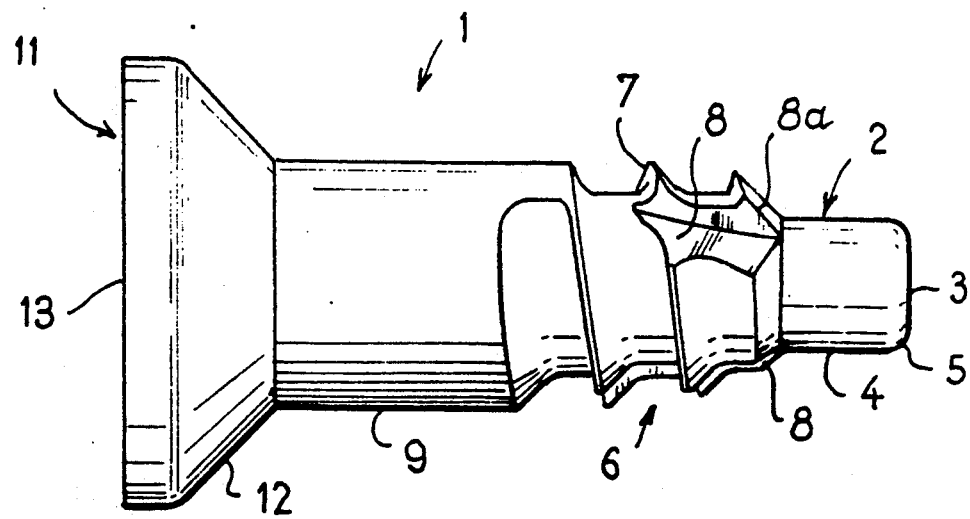
FIG. 2 is a side view on the same scale as FIG. 1 of the screw according to the invention.

The length (1) of the dog point 2 is at least equal to its diameter (d) (substantially greater than d in FIG. 1 to 3).

In the screw 1 there is made an axial hollow 15 extending from the head 11, constituted by a housing 16 which is limited by the surface 13 and profiled in order to receive a screwing tool, and by an axial bore 17 which extends the housing 16 in the direction of the terminal dog point 2. The bore 17 is adapted in order to receive equipment for joining to an article which is to be supported by screws 1 anchored on the patient, such as the article 19 for interface with the stereotaxy frame 10 (FIG. 6 and FIG. 7).

Figure 8:
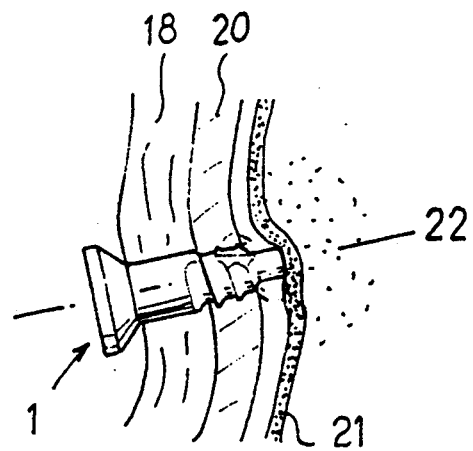
FIG. 8 is a view which is a half partial section and half elevation of the wall of the neurocranium and of a screw anchored in the latter, ready to receive a frame such as the one in FIG. 5 and FIG. 6.

In the case of the use of the screw 1 according to the invention as a support for a stereotaxy frame 10, the neurosurgeon or doctor who places the necessary screws 1 anchors them in succession in the wall of the bone 20 with an inclination demanded by the frame 10 on the surface of the skin 18 (see FIG. 8) and of the cranial bone 19. During the screwing, the self-tapping part 8 bores and taps the necessary passage hole in the neurocranium 20, then the rounded dog point 2, after having passed through the bone 20, slightly pushes the dura mater 21 back. The latter locally takes the position represented in FIG. 8 without damage to it, and consequently without risk by the introduction of the screw 1 of causing a lesion of the subjacent organs 22. The boring of the neurocranium 20 by the self-tapping part 8 and the threaded zone 6 are capable of causing the appearance of bone splinters, which should not injure the dura mater 21. This result is made possible by the rounded shape of the terminal dog point 2, which gently pushes the dura mater 21 back without provoking any harm to it and moves the splinters apart under its pressure.

Figure 7:
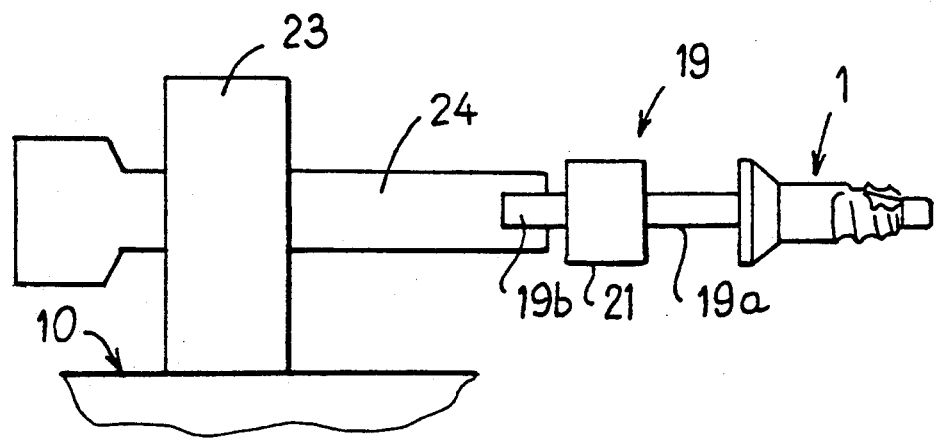
FIG. 7 is a view in partial elevation of the frame and of one of the screws of the device of FIG. 5 and FIG. 6.

For their part, the smooth parts 9 and 12, in contact with the skin 18 are not capable of damaging the latter with which they remain in contact in their final position, as represented in FIG. 7 in which the head 11 juts out from the skin 18.

The choice of the arrangement of the smooth parts 9 and 12 allows, taking into account the inclination of the screws 1 demanded by its frame 10, the skin of the cranium 18 not to be damaged and good support on the neurocranium 20 to be provided.

This solid anchoring therefore allows easy repositioning of a frame such as 10, for the purposes of the planned investigations.

The joining equipment between the frame 10 and the screws 1 comprise in the example illustrated in FIG. 6 and FIG. 7, an interface article 19 fitted with a central disc 21 on either side of which two anterior 19a and posterior 19b parts jut out axially. An interface article such as 19 allows a frame 10 be mounted on the screws 1 using four corner pillars 23 fixed to the frame and which each carry a transverse barrel 24 drilled on either side with an axial hole for receiving the posterior part 19a.

In order to place a screw 1 in the cranium 20 of the patient, the surgeon introduces a screwdriver axially in the barrel 24 placed on its support pillar 23, performs the screwing, removes the screwdriver, and places the interface article 19 between the screw 1 and the barrel 24 by introducing therein respectively the parts 19a and 19b.

After having carried out the planned examinations and investigations, the neurosurgeon removes the frame 10 and the joining equipment 19, the screws 1 remaining anchored in place until the next examination.

The percutaneous screws 1 are advantageously made of titanium, which makes it possible not to deform the radiological or MRI images (Artefact).

In the scope of its use as a support for a stereotaxic system such as 10, the screw 1 according to the invention has the abovementioned advantages, which are of particular interest for the various applications of stereotaxy: diagnosis of cerebral lesions, their locating for their subsequent multi-beam irradiation, treatment of benign lesions, placing stimulators in the brain, or electrodes in order to find the positions from where electrical discharges come during epileptic fits etc.

The invention is not limited to the embodiment described and can include other embodiments. The number of self-tapping grooves 8 can thus vary: there are in particular advantageously three of them, angularly separated by approximately 120 degrees.

Moreover, the rounded shape of the dog point 2 may vary widely: it may also in particular be spherical or conical with a rounded apex. The screw illustrated in the drawings may be modified by replacing the cylindrical lateral surface 4 by a conical or spherical surface. The self-tapping zone may also be removed from the screw.

I claim:

1. A percutaneous bone screw (1) for supporting a stereotaxy frame (10) on the cranium of a patient comprising:
    a threaded part (6) having a self-tapping zone which is constituted by at least one groove formed by a flat (8) bordered by sharp edges (8a) which terminates adjacent one end of said threaded part, and a non-threaded dog point (2) contiguous with said one end, said dog point (2) having a plane transverse surface (3) and a cylindrical lateral surface (4) connected to said plane surface by a rounded annular radius (5), said transverse surface having a diameter substantially equal to the diameter of said cylindrical lateral surface.

2. The screw according to claim 1 wherein said threaded part (6) has three self-tapping zones (8) angularly separated by approximately 120 degrees.

3. The screw according to claim 2 further comprising a head opposite said dog point, a smooth cylindrical part (9), arranged between said threaded part (6) and said head (11) adapted to receive a manipulating tool.

4. The screw according to claim 3 wherein said smooth cylindrical part (9) is connected to said head of the screw (1) by an annular zone (12) which is inclined with respect to a longitudinal axis (XX) of the screw.

5. The screw according to claim 4 further comprising an axial hollow (15) extending from said head (11), constituted by a housing (16) which is profiled in order to receive a screwing tool, and by an axial bore (17) which extends in the direction of said dog point (2), said bore being adapted to receive equipment (18) for joining to a stereotaxy frame (10).

6. The screw according to claim 1 wherein said dog point (2) has a length that is equal to or greater than the diameter of said cylindrical lateral surface.

* * * * *